United States Patent [19]

Kume et al.

[11] Patent Number: 5,342,938
[45] Date of Patent: Aug. 30, 1994

[54] BENZOXAZINE INTERMEDIATES

[75] Inventors: Toyohiko Kume, Hino; Toshio Goto, Shimotsuga; Atsumi Kamochi, Oyama; Hidenori Hayakawa, Oyama; Akihiko Yanagi, Oyama; Tadao Asami, Oyama, all of Japan

[73] Assignee: Nihon Bayer Agrochem K.K., Tokyo, Japan

[21] Appl. No.: 14,022

[22] Filed: Feb. 5, 1993

Related U.S. Application Data

[62] Division of Ser. No. 761,199, Sep. 16, 1991, Pat. No. 5,207,818.

[30] Foreign Application Priority Data

Sep. 25, 1990 [JP] Japan ................. 2-251839

[51] Int. Cl.⁵ ............................ C07D 265/36
[52] U.S. Cl. .................................... 544/105
[58] Field of Search ........................ 544/105

[56] References Cited

FOREIGN PATENT DOCUMENTS 2206018 8/1973 Fed. Rep. of Germany ...... 544/105
60-126274 7/1985 Japan ................................ 544/105

OTHER PUBLICATIONS

Quiroz et al, Heterocycles, vol. 32, No. 9, (1991), pp. 1681–1685.

Primary Examiner—Mukund J. Shah
Assistant Examiner—P. I. Datlow
Attorney, Agent, or Firm—Sprung Horn Kramer & Woods

[57] ABSTRACT

Novel benzoxazines of the formula (I)

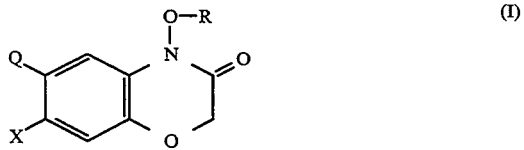

the use of the new compounds as herbicides, and novel compounds of the formula (IX) as intermediates

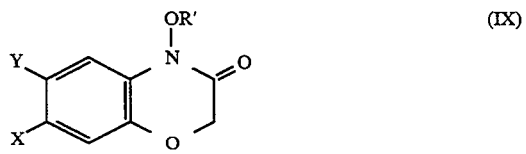

are disclosed.

4 Claims, No Drawings

BENZOXAZINE INTERMEDIATES

This is a division of application Ser. No 07/761,199 filed Sep. 16, 1991, now U.S. Pat. No. 5,207,818.

The present invention relates to novel benzoxazines, to processes for their preparation, to their use as herbicides as well as to novel intermediates for their preparation and to process for their preparation.

It has already been disclosed that benzoxazine derivatives have herbicidal properties (e.g. see U.S. Pat. No. 4,640,707, U.S. Pat. No. 4,729,784, Japanese Patent Laid-open NO. 138,183/1990).

There have now been found novel benzoxazines of the formula (I)

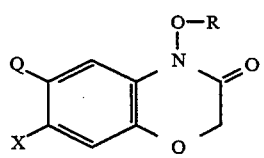

wherein Q represents

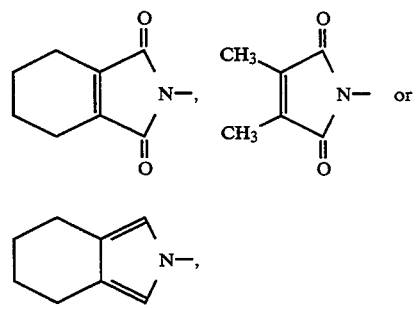

X represents a hydrogen atom or fluorine atom, and R represents a $C_{1-5}$ alkyl group, $C_{3-4}$ alkenyl group, $C_{3-4}$ alkynyl group, cyclopropylmethyl group, $C_{2-3}$ cyanoalkyl group, $C_{1-2}$ alkoxy-$C_{1-2}$ alkyl group or $C_{1-2}$ alkylthio-$C_{1-2}$ alkyl group.

The compounds of the formula (I) can be obtained by a process in which a) : where Q represents the following group;

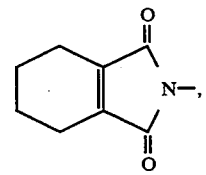

compounds of the formula (II)

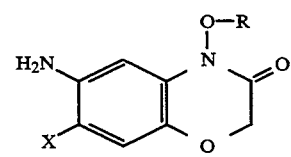

wherein X and R have the same meanings as mentioned before, are reacted with 3,4,5,6-tetrahydrophtalic anhydride in the presence of an inert solvent, or b) : where Q represents the following group;

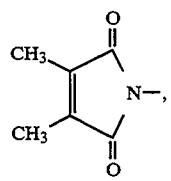

the aforesaid compounds of the formula (II) are reacted with 2,3-dimethylmaleic anhydride in the presence of an inert solvent, or c) : where Q represents the following group;

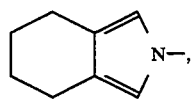

the aforesaid compounds of the formula (II) are reacted with 1,2-cyclohexanedicarboxyaldehyde in the presence of an inert solvent and if appropriate, in the presence of a catalyst.

The benzoxazines, according to the present invention exhibit a strong herbicidal activities.

In the formulae, $C_{1-5}$ alkyl represents methyl, ethyl, propyl, iso-propyl, n-(iso-, sec-, or tert-) butyl, pentyl, or iso-pentyl, preferably methyl, ethyl, propyl, iso-propyl, or n-(iso-, sec-, or tert-) butyl, and particularly-methyl or ethyl.

$C_{3-4}$ alkenyl represents allyl or 1-propenyl and preferably allyl.

$C_{3-4}$ alkynyl represents propargyl or 1-methyl-2-propynyl, and preferably propargyl.

The alkyl part in $C_{2-3}$ cyanoalkyl represents $C_{1-2}$ alkyl, and preferably methyl.

The $C_{1-2}$ alkyl part in $C_{1-2}$ alkoxy-$C_{1-2}$ alkyl and $C_{1-2}$ alkylthio-$C_{1-2}$ alkyl represents preferably methyl.

Among the compounds of the formula (I), according to the invention, preferred compounds are those in which Q represents the following groups;

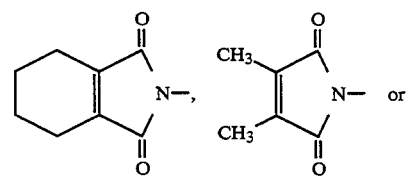

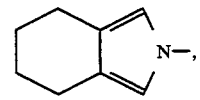

X represents fluorine,

R represents $C_{1-3}$ alkyl, allyl, propargyl, 1-methyl-2-propynyl, cyclopropylmethyl, cyanomethyl, methoxymethyl, or methylthiomethyl.

Particularly preferred compounds of the formula (I) are those in which

Q represents the following group;

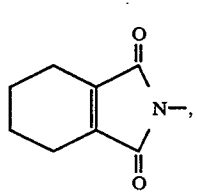

X represents fluorine, and

R represents methyl, ethyl, allyl, propargyl, cyclopropylmethyl, cyanomethyl, methoxymethyl, or methylthiomethyl.

If, for example, in the process a), 6-amino-4-ethoxy-7-fluoro-1,4-benzoxazin-3(4H)-one and 3,4,5,6-tetrahydrophthalic anhydride are used as starting materials, the course of the reaction can be represented by the following equation:

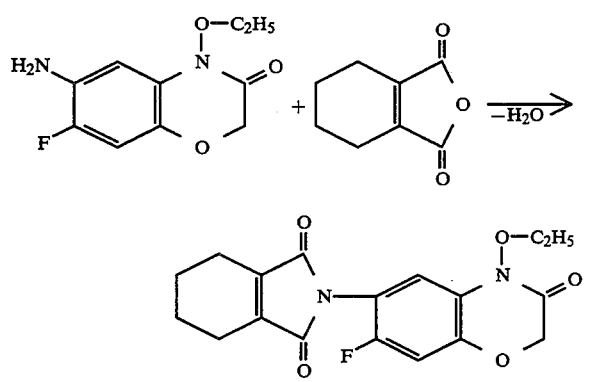

If, for example, in the process b), 6-amino-4-ethoxy-7-fluoro-1,4-benzoxazin-3(4H)-one and 2,3-dimethylmaleic anhydride are used as starting materials, the course of the reaction can be represented by the following equation:

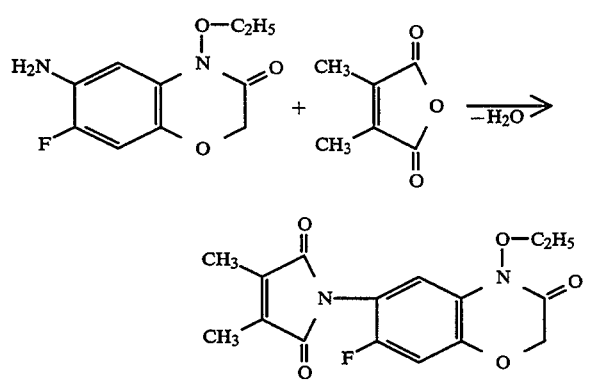

If, for example, in the process c), 6-amino-4-ethoxy-7-fluoro-1,4-benzoxazin-3(4H)-one and 1,2-cyclohexanedicarboxaldehyde are used as starting materials, the course of the reaction can be represented by the following equation:

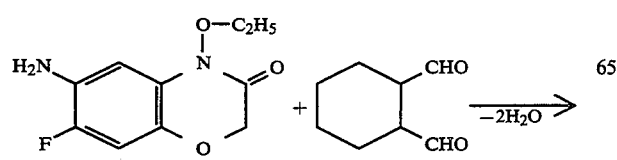

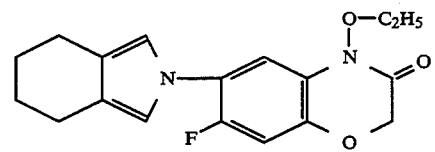

The compounds of the formula (II) as a starting material, in the processes a), b) and c) mean ones based on the aforementioned definitions of X and R.

Preferably, the compounds of the formula (II) are defined, according to the definitions of X and R in the aforesaid preferred compounds of the formula (I).

The compounds of the formula (II) are novel and can be obtained by a process in which d) : compounds of the formula (III)

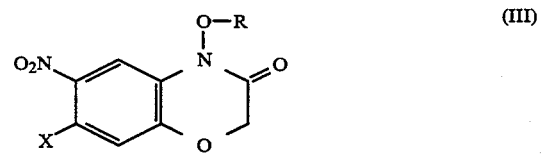

wherein X and R have the same meanings as mentioned before, are reduced in the presence of an inert solvent.

The reduction reaction in the process d) can be readily carried out by hydrogenation with the use of catalytic amount of palladium-carbon or with the use of nascent hydrogen in the presence of iron-acetic acid.

The compounds of the formula (III) are also novel and can be obtained by a process in which e) : compounds of the formula (IV)

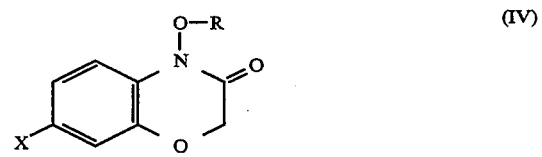

wherein X and R have the same meanings as mentioned before, are nitrated.

The process e) can be carried out according to nitration reaction that is disclosed in "Synthetic Organic Chemistry" by R. B. Wagner and H. D. Zook, page 746, published in ]1953 by John Wiley & Sons Inc.

The compounds of the formula (IV) are also novel and can be obtained by a process in which f) : compounds of the formula (V)

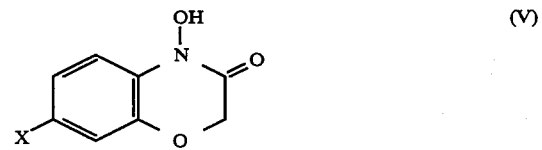

wherein X has the same meaning as mentioned before, are reacted with compounds of the formula (VI)

wherein R has the same meaning as mentioned before and L represents bromo, chloro, iodo, or —SO$_2$M, wherein M represents methyl, phenyl or p-tolyl, in the presence of an inert solvent.

The process f) is known in itself.

The above compounds of the formula (V) can be obtained by a process in which g) : compounds of the formula (VII)

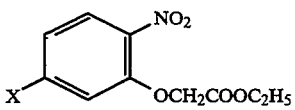
(VII)

wherein X has the same meaning as mentioned above, are cyclized.

The compounds of the formula (VI) are well-known in the field of organic chemistry.

The above-mentioned process g) can be carried out according to the process disclosed in "Synthesis" 1989, pages 211–212.

The above compounds of the formula (VII) are known and can be obtained by a process in which h) : compounds of the formula (VIII)

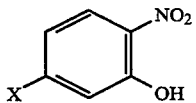
(VIII)

wherein X has the same meaning as mentioned before, are reacted with ethyl bromoacetate.

The compounds of the formula (VIII) and ethyl bromoacetate are both well-known.

The process h) can be carried out according to the process disclosed in "Synthesis" 1989, pages 211 to 212.

The starting materials in the processes a), b) and c), viz., 3,4,5,6-tetrahydrophthalic anhydride, 2,3-dimethylmaleic anhydride and 1,2-cyclohexanedicarboxyaldehyde, respectively, are known compounds.

In the above-mentioned respective processes, the resulting novel intermediate compounds can be defined under the following general formula:

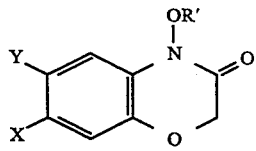
(IX)

wherein Y represents a hydrogen atom, nitro group, or amino group.

X represents a hydrogen atom or fluorine atom and R' represents a hydrogen atom, C$_{1-5}$ alkyl group, C$_{3-4}$ alkenyl group, C$_{3-4}$ alkynyl group, cyclopropylmethyl group, C$_{2-3}$ cyanoalkyl group, C$_{1-2}$ alkoxy-C$_{1-2}$ alkyl group, or C$_{1-2}$ alkylthio-C$_{1-2}$ alkyl group with the proviso that X and Y each do not represent a hydrogen atom at the same time.

As appropriate diluents for carrying out the process a) may be mentioned any kind of inert solvents.

As the example of such solvents may be mentioned water, aromatic hydrocarbons such as ethylene chloride, benzene, toluene, xylene, chlorobenzene, dichlorobenzene, and biphenyl, for example; ethers such as dioxane and diphenyl ether, for example; alcohols such as ethanol, isopropanol, butanol, and ethylene glycol, for example; organic acids such as, for example, acetic acid, propionic acid, etc.

The above-mentioned process a) can be carried out in a substantially wide range of temperature. For example, use may be made of temperatures from about 70° C. to about 280° C., preferably from about 80° C. to about 140° C.

The reaction is preferably carried out at normal pressure but higher or reduced pressure may also be used.

In carrying out the process a), the desired compounds of the formula (I) can be obtained by reacting about 1 to about 1.2 mols of 3,4,5,6-tetrahydrophthalic anhydride with 1 mol of the compounds of the formula (II), for example, in the presence of acetic acid.

In carrying out the above-mentioned process b), use may be made, as suitable diluents, of the same inert solvents as mentioned in the afore-mentioned process a).

The process b) can be carried out in a substantially wide range of temperature. For example, the process is carried out at a temperature in the range of from about 70° C. to about 280° C., preferably from about 80° C. to about 100° C.

The reaction may be carried out at normal pressure but higher or reduced pressure may also be used.

In carrying out the process b), the desired compounds of the formula (I) can be obtained by reacting from about 1 to about 1.2 mols of 2,3-dimethylmaleic anhydride with 1 mol of the compounds of the formula (II), for example, in the presence of acetic acid.

In carrying out the process c), use may be made, as suitable diluents, of benzene, toluene, zylene, dioxane and alcohols having a boiling point not lower than 100° C. such as tert.-butanol, tert.-amylalcohol etc., and polyoxyalkanes such as 1,2-dimethoxyethane etc.

The process c) can be carried out in the presence of catalysts and as the examples thereof, may be mentioned organic acids such as paratoluene sulfonic acid, for example, inorganic acids such as concentrated sulfuric acid, solid phase acidic catalysts such as ion exchange resins, silica gel, etc.

The process c) can be carried out in a substantially wide range of temperature. For example, the process is carried out at a temperature in the range of from about 60° C. to about 250° C., preferably from about 100° C. to about 140° C.

The reaction may be carried out at normal pressure but higher or reduced pressure may also be used.

In carrying out the process c), the desired compounds of the formula (I) can be obtained by reacting from about 1 to about 1.1 mols of 1,2-cyclohexanedicarboxyaldehyde with 1 mol of the compounds of the formula (II), for example, in the presence of an inert solvent, and under heat-refluxing as shown in the following examples.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Ablution, Emex, Datura, Viola, Galeopsis, Papaver and Centaurea.

Dicotyledon cultures of the genera

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera

Oryza, Zea, Triticum, Hordeurn, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted into the customary formulations, such as solutions, emulsions, wettable powders, suspensions, powders, foams, pastes, granules, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in a known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents, diluents or carriers, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethyl-sulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural ,and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 per cent by weight of active compound, preferably from 0.5 to 90 per cent by weight.

The active compounds according to the invention, as such or in the form of their formulations, can also be used, for combating weeds, as mixtures with known herbicides, finished formulations or tank mixes being possible.

Possible components for the mixture are known herbicides, such as, for example, 4-amino-6-(1,1-dimethylethyl)-3-ethylthio-1,2,4-triazin-5(4H)-one, 1-amino-6-ethylthio-3-(2,2-dimethylpropyl)1,3,5-triazine-2,4(1H,3H)-dione or N-(2-benzothiazolyl)-N,N'-dimethyl-urea, for combating weeds in cereals; 4-amino-3-methyl-6-phenyl-1,2,4-triazin-5(4H)-one for combating weeds in sugar beet and 4-amino-6-(1,1-dimethylethyl)-3-methylthio-1,2,4-triazin -5(4H)-one for combating weeds in soya bean. Surprisingly, some mixtures also show a synergistic action.

Mixtures with other known active compounds, such as herbicides, fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing. They are used, in particular, after emergence of the plants.

The amount of active compound used can vary within a substantial range. It depends essentially on the nature of the desired effect. In general, the amounts used are between 0.001 and 5 kg of active compound per hectare of soil surface, preferably between 0.01 and 2 kg per ha.

The preparation and use of the active compounds according to the invention can be seen from the following examples.

PREPARATIVE EXAMPLES

Example 1

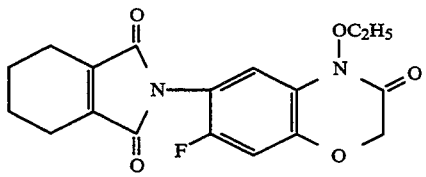

A mixture consisting of 6-amino-4-ethoxy-7-fluoro-1,4-benzoxazin -3(4H)-one (3 g), acetic acid (25 g), and 3,4,5,6-tetrahydrophthalic anhydride (2.02 g) was stirred for one hour under heat-refluxing.

After having been allowed to cool, the resulting reaction product was distilled under reduced pressure to remove the acetic acid therefrom and, after addition of toluene (100 ml) to the .residue, was stirred and filtered. The filtrate was washed with saturated aqueous solution of sodium carbonate, and water, in that order, followed by drying with magnesium sulfate.

The solvent was distilled off under reduced pressure and the residue was purified through silica-gel chromatography (eluent: toluene/tetrahydrofuran=5/1), followed by recrystallization from ethanol to obtain the aimed 4-ethoxy-7-fluoro-6-(4,5,6,7-tetrahydro-2H-isoindole -1,3-dion-2-yl)-1,4-benzoxazin-3(4H)-one (2.8 g) having a m.p. in the range of from 151° to 152° C.

Example 2

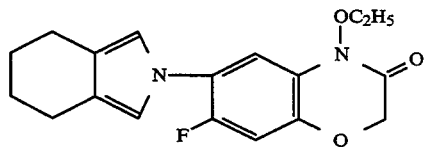

A mixture consisting of 6-amino-4-ethoxy-7-fluoro-1,4-benzoxazin -3(4H)-one (1.06 g), 1,2-cyclohexanedicarboxyaldehyde (0.7 g) and xylene (50 ml) was stirred for 15 minutes under heat-refluxing. After the solvent had been distilled off under reduced pressure, the residue was purified through silica-gel chromatography (eluent: hexane/ethyl acetate=19/1) to obtain the aimed 4-ethoxy-7-fluoro-6-(4,5,6,7-tetrahydroisoindole-2-yl)1,4-benzoxazin-3(4H)-one (1.37 g). $n_D^{20}$ 1.5797

The compounds according to the present invention, which may be obtained in the same way as those of the afore-mentioned Examples 1 and 2 are demonstrated in the Table 1, including those obtained in the aforementioned Examples 1 and 2.

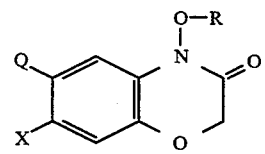

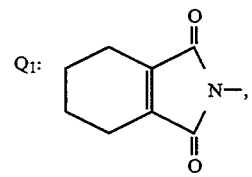

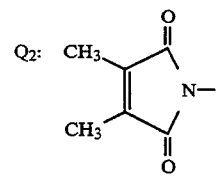

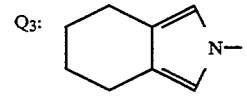

TABLE 1

| Compound No. | Q | X | R | mp. (°C.)/$n_D^{20}$ |
|---|---|---|---|---|
| 1 | $Q_1$ | H | $C_2H_5$ | 164–166 |
| 2 | $Q_2$ | H | $C_2H_5$ | |
| 3 | $Q_1$ | F | $CH_3$ | 146–149 |
| 4 | $Q_1$ | F | $C_2H_5$ | 151–152 |
| 5 | $Q_2$ | F | $C_2H_5$ | 150–151 |
| 6 | $Q_3$ | F | $C_2H_5$ | 1.5797 |
| 7 | $Q_1$ | F | $C_3H_7$-iso | |
| 8 | $Q_1$ | F | $C_3H_7$-n | |
| 9 | $Q_1$ | F | $CH_2CH=CH_2$ | |
| 10 | $Q_1$ | F | $CH_2C\equiv CH$ | 150–151 |
| 11 | $Q_3$ | F | $CH_2C\equiv CH$ | rubbery |
| 12 | $Q_1$ | F | $\underset{CHC\equiv CH}{\overset{CH_3}{\|}}$ | |
| 13 | $Q_1$ | F | $CH_2C\equiv CH$ | |
| 14 | $Q_1$ | F | $CH_2OCH_3$ | |
| 15 | $Q_1$ | F | $CH_2SCH_3$ | |
| 16 | $Q_1$ | F | $CH_2-\triangleleft$ | |

Example 3 (Synthesis of Material Compound)

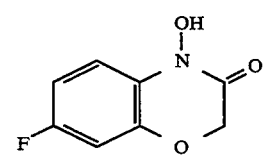

To a mixture consisting of 5-fluoro-2-nitrophenol (47.1 g), acetonitrile (300 ml) and potassium carbonate (46 g) was added ethyl bromoacetate (60.1 g) dropwise at a temperature from 50° to 60° C., followed by a five-hour refluxing under heating and then filtration under cooling. The resulting filtrate was subjected to distillation under reduced pressure, and then dissolved in toluene (350 ml). The resulting toluene solution was washed with water, a 5% aqueous solution of potassium hydroxide, and water, in that order, followed by drying with magnesium sulfate and the toluene was distilled off therefrom under reduced pressure. The residue was distilled under reduced pressure to collect a fraction boiling at from 154° to 156° C., so as to obtain ethyl 5-fluoro-2-nitrophenoxyacetate (65.3 g ). The whole quantity of the reaction product was dissolved in ethanol (1.8 l), followed by addition thereto of a solution of ammonium chloride (60 g) and water (400 ml). To the resulting mixture was added zinc dust (60.5 g) portionwise at a temperature of from 20° to 30° C.

After the exothermic reaction having ceased, a two-hour stirring was continued at a temperature from 30° to 40° C. The solids collected by filtration were extracted with 2N- sodium hydroxide (200 ml×3). The resulting alkaline extract was acidified with the use of concentrated hydrochloric acid under ice-cooling. The resulting solids were filtered, washed with ice water, dried and then recrystallized from aqueous ethanol, to obtain the aimed 7-fluoro-4-hydroxy-1,4-benzoxazin-3(4H)-one (20.5 g) having a m.p. in the range of from 183°–184° C.

Example 4 (Synthesis of Material Compound)

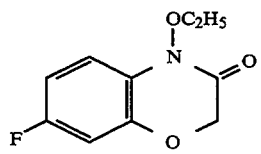

A mixture consisting of 7-fluoro-4-hydroxy-1,4-benzoxazin-3(4H)-one (11 g), acetonitrile (160 g), potassium carbonate (9.1 g) and iodo ethane (10.9 g) was stirred for six hours under heat-refluxing, followed by cooling and then distillation at reduced pressure. To the resulting residue were added ethyl acetate (150 ml) and water (100 ml), followed by stirring. The ethyl acetate layer was separated and it was washed with a 5% aqueous solution of potassium hydroxide, water and water saturated with sodium chloride in that order, followed by drying sodium sulfate.

After distillation under reduced pressure, the residue was recrystallized from n-hexane, to obtain the aimed 4-ethoxy-7-fluoro -1,4-benzoxazin-3(4H )-one (8.6 g) having a m.p. in the range of from 61° to 62° C.

Example 5 (Synthesis of Material Compound)

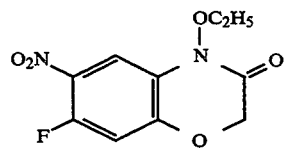

4-ethoxy-7-fluoro-1,4-benzoxazin-3(4H)-one (9.1 g) was added to sulfuric acid (100 ml) that had been cooled to a temperature in the range of from 0° to 5° C., followed by dropwise addition thereto of a 98% nitric acid (2.8 g) at a temperature not higher than 0° C.

After a one-hour stirring at 0° to 5° C., the reaction mixture was poured onto ice and extracted with ethyl acetate (50 ml×2). The resulting ethyl acetate extract was washed with water, saturated aqueous sodium hydrogen carbonate, water, and saturated aqueous sodium chloride, in that order, followed by drying with magnesium sulfate. The residue obtained by distillation at reduced pressure was recrystallized by using a solvent mixture comprising toluene-hexane, to obtain the aimed 4-ethoxy-7-fluoro-6-nitro-1,4-benzoxazin-3(4H )-one (9.6 g) having a m.p. in the range of from 108° to 110° C.

Example 6

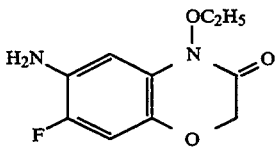

4-ethoxy-7-fluoro-6-nitro-1,4-benzoxazin-3(4H)-one (6.83 g) was portionwise added to a mixture consisting of iron powder (6.55 g), acetic acid (3.3 g), water (28 ml) and ethanol (20 ml) at a temperature in the range of from 70° C. to 80° C., followed by a continuous two-hour stirring thereof under heat-refluxing.

Under reduced pressure, the ethanol and water were distilled off from the reaction mixture and to the residue was added ethyl acetate (200 ml), followed by stirring and then filtration. The resulting filtrate was washed with saturated aqueous sodium hydrogen carbonate, water, and saturated aqueous sodium chloride, in that order, followed by drying with sodium sulfate.

The solvent was distilled off from the reaction product, to obtain the aimed 6-amino-4-ethoxy-7-fluoro-1,4-benzoxazin-3(4H)-one (5.4 g) having a m.p. in the range of from 76° to 80° C.

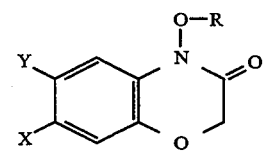

| Compound No. | Y | X | R | mp. (°C.) |
|---|---|---|---|---|
| IX-1 | H | F | H | 183–184 |
| IX-2 | H | F | CH$_3$ | 74–75 |
| IX-3 | NO$_2$ | F | CH$_3$ | 190–195 |
| IX-4 | NH$_2$ | F | CH$_3$ | 149–151 |
| IX-5 | H | F | C$_2$H$_5$ | 58–60 |
| IX-6 | NO$_2$ | F | C$_2$H$_5$ | 108–110 |
| IX-7 | NH$_2$ | F | C$_2$H$_5$ | 76–80 |
| IX-8 | H | F | C$_3$H$_7$-iso | |
| IX-9 | H | F | C$_3$H$_7$-n | |
| IX-10 | H | F | CH$_2$CH=CH$_2$ | |
| IX-11 | H | F | CH$_2$C≡CH | 131–132 |
| IX-12 | NO$_2$ | F | CH$_2$C≡CH | 121–123 |
| IX-13 | NH$_2$ | F | CH$_2$C≡CH | 169–171 |
| IX-14 | H | F | CH$_2$N | |
| IX-15 | H | F | CH$_2$OCH$_3$ | |
| IX-16 | H | F | CH$_2$SCH$_3$ | |
| IX-17 | H | F | CH$_2$—◁ | |
| IX-18 | NO$_2$ | H | C$_2$H$_5$ | |
| IX-19 | NH$_2$ | H | C$_2$H$_5$ | 70–73 |

Biotest Example

Formulation of Active Compounds

Carrier: 5 parts by weight of acetone

Emulsifier: 1 part by weight of benzyloxy polyglycol ether

To produce a suitable formulation of each of the active compounds, 1 part by weight of the active compound was mixed with the stated amount of carrier and with the stated amount of emulsifier, and the resulting emulsifiable concentrate was then diluted with water to the desired concentrations.

| Rating | Assessment on Herbicidal Effect |
|---|---|
| | Herbicidal effect of active compound on weed in %* |
| 5 | 95% or more (killed) |
| 4 | at least 80% and less than 95% |
| 3 | at least 50% and less than 80% |
| 2 | at least 30% and less than 50% |
| 1 | at least 10% and less than 30% |
| 0 | less than 10% (no herbicidal effect) |
| | Phytotoxic effect of active compound on crops in %* |
| 5 | at least 90% (fatal phytotoxicity) |
| 4 | at least 50% and less than 90% |
| 3 | at least 30% and less than 50% |
| 2 | at least 10% and less than 30% |
| 1 | more than 0% and less than 10% |
| 0 | 0% (no phytotoxicity) |

*Above-mentioned values (%) are those obtained by comparing the test data in the treated section with the test data in the control (untreated) section.

The kinds of weeds under test
A: Barnyard grass (*Echinochloa crus-galli*)
B: Wild amaranth (*Amaranthus lividus L.*)
C: Goosefoot (*Chenopodium album L.*)
D: Polygonum (*Polygonum blumei L.*)
E: Putslane (*Portulaca oleracea L.*)

Comparative Compound

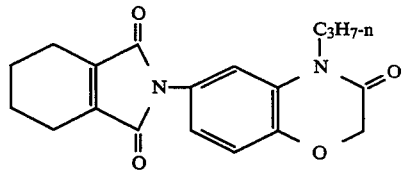

Disclosed in U.S. Pat. No. 4640707 specification

Example 7 (Test on upland farm weeds by foliar treatment) emergence:-)

In a greenhouse, wheat seeds were sown in 500 cm² pots filled with upland farm soil, and soil containing seeds of Barnyard grass (*Echinochloa cruss-galli*), Wild amaranth (*Amaranthus lividus L.*), goosefoot (*Chenopodium album L.*), Polygonum and Purslane (*Portulaca oleracea L.*) was put over the soil in the pots in a depth of 1 cm.

After sowing, the plants were grown for 14 days and a test chemical in a predetermined concentration was uniformly sprayed over the test plants in each of the test pots.

Four weeks after the spraying, the herbicidal effect and the phytotoxicity to crops were examined.

Example 8 (Test on upland weeds by soil treatment before emergence:-)

In a greenhouse, wheat seeds were sown in 500 cm² pots filled with upland farm soil, and soil containing seeds of the same weeds as in Example 7 was put over the soil in the pots in a depth of 1 cm.

One day after sowing, a test chemical in a predetermined concentration was uniformly sprayed over the surface layer of the soil in each of the test pots.

Four weeks after the spraying, the herbicidal effect and the phytotoxicity to crops were examined.

The results of Examples 7 and 8 are shown in Table 3.

TABLE 3

| Compound No. | Amount of active compound kg/ha | Herbicidal Effect | | | | | | | | | | | |
|---|---|---|---|---|---|---|---|---|---|---|---|---|---|
| | | foliage application | | | | | | soil treatment | | | | | |
| | | A | B | C | D | E | Wheat | A | B | C | D | E | Wheat |
| 1 | 0.1 | 3 | 5 | 5 | 5 | 5 | 1 | 3 | 5 | 5 | 5 | 5 | 0 |
| 3 | 0.1 | 3 | 5 | 5 | 5 | 5 | 0 | 3 | 5 | 5 | 5 | 5 | 0 |
| 4 | 0.1 | 4 | 5 | 5 | 5 | 5 | 0 | 4 | 5 | 5 | 5 | 5 | 0 |
| 5 | 0.1 | 3 | 4 | 4 | 5 | 5 | 0 | 3 | 4 | 4 | 5 | 5 | 0 |
| 6 | 0.1 | 3 | 5 | 5 | 5 | 5 | 0 | 3 | 5 | 5 | 5 | 5 | 0 |
| 10 | 0.1 | 3 | 5 | 5 | 5 | 5 | 0 | 4 | 5 | 5 | 5 | 5 | 0 |
| 11 | 0.1 | 3 | 5 | 5 | 5 | 5 | 0 | 3 | 5 | 4 | 5 | 5 | 0 |
| Comparative C-1 | 0.1 | 3 | 5 | 4 | 5 | 5 | 3 | 2 | 4 | 3 | 4 | 4 | 3 |

What is claimed is:
1. A benzoxazine of the formula (IX)

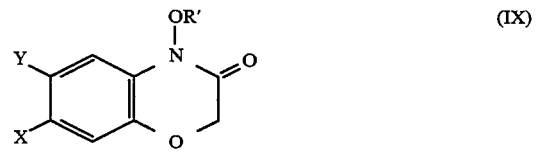

wherein Y represents a hydrogen atom, nitro group, or amino group,

X represents fluorine atom and

R' represents $C_{1-5}$ alkyl group, $C_{3-4}$ alkenyl group, $C_{3-4}$ alkynyl group, cyclopropylmethyl group, $C_{2-3}$ cyanoalkyl group, $C_{1-2}$ alkoxy-$C_{1-2}$ alkyl group, or $C_{1-2}$ alkylthio-$C_{1-2}$ alkyl group.

2. The benzoxazine of the formula (IX) according to claim 1, wherein X, Y and R' are:

| Y | X | R' |
|---|---|---|
| H | F | $CH_3$ |
| $NO_2$ | F | $CH_3$ |
| $NH_2$ | F | $CH_3$ |
| H | F | $C_2H_5$ |
| $NO_2$ | F | $C_2H_5$ |
| $NH_2$ | F | $C_2H_5$ |
| H | F | $C_3H_7$-iso |
| H | F | $C_3H_7$-n |
| H | F | $CH_2CH\!=\!CH_2$ |
| H | F | $CH_2C\!\equiv\!CH$ |
| $NO_2$ | F | $CH_2C\!\equiv\!CH$ |
| $NH_2$ | F | $CH_2C\!\equiv\!CH$ |

-continued
| Y | X | R' |
|---|---|---|
| H | F | CH$_2$N |
| H | F | CH$_2$OCH$_3$ |
| H | F | CH$_2$SCH$_3$ |
| H | F | CH$_2$—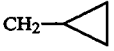 |
3. A benzoxazine of the formula (IX)
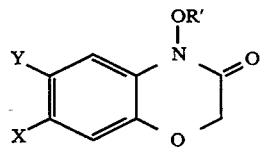
wherein Y represents a hydrogen atom, nitro group or amino group,
X represents a fluorine atom and
R' represents a hydrogen atom.
4. The benzoxazine of the formula (IX) according to claim 3, wherein X, Y and R' are:
| Y | X | R' |
|---|---|---|
| H | F | H |
* * * * *